United States Patent [19]

Lombardo et al.

[11] Patent Number: 4,856,512
[45] Date of Patent: Aug. 15, 1989

[54] LASER HEAD AND MICROSCOPE ATTACHMENT ASSEMBLY WITH SWIVEL CAPABILITY

[75] Inventors: Igino Lombardo, Sharon; Richard L. Walus, Norwell, both of Mass.

[73] Assignee: I.L.Med, Inc., Walpole, Mass.

[21] Appl. No.: 179,819

[22] Filed: Apr. 11, 1988

[51] Int. Cl.⁴ .............................................. A61B 17/36
[52] U.S. Cl. .................................. 128/303.1; 128/395; 219/121.61
[58] Field of Search ...................... 128/303.1, 395, 396; 219/121.61; 372/108

[56] References Cited

U.S. PATENT DOCUMENTS

| | | | |
|---|---|---|---|
| 3,084,694 | 4/1963 | Kavanagh et al. | 128/303.1 |
| 3,348,547 | 10/1967 | Kavanagh | 128/395 |
| 4,491,131 | 1/1985 | Vassiliadis | 128/303.1 |
| 4,494,540 | 1/1985 | Erb | 128/303.1 |
| 4,622,967 | 11/1986 | Schachar | 128/303.1 |

*Primary Examiner*—Lee S. Cohen
*Attorney, Agent, or Firm*—Weingarten, Schurgin, Gagnebin & Hayes

[57] ABSTRACT

A microscope attachment assembly for mounting a portable surgical laser directly to a surgical microscope to permit the laser to be rotated with respect to the optical axis of the microscope to various physical positions so that if the position of laser obstructs visual or physical axis to the surgical site it may be quickly and conveniently moved with a minimum risk of misalignment.

17 Claims, 4 Drawing Sheets

LASER HEAD AND MICROSCOPE ATTACHMENT ASSEMBLY WITH SWIVEL CAPABILITY

FIELD OF THE INVENTION

The present invention relates to a laser head and microscope attachment assembly and more particularly to an assembly which permits a laser to be rotated with respect to the microscope to which the assembly is typically attached.

BACKGROUND OF THE INVENTION

In microsurgical applications, a surgical laser may be used in conjunction with a surgical microscope. Small laser heads have been developed which can mount directly to a surgical microscope usually by attaching directly to the standard microscope dovetail mount or to the standard microscope objective lens mount. Two types of microscope mounted lasers have been used. Some are mounted with the laser extending at about 90° with respect to the microscope optical axis and others are mounted with the laser extending parallel to the microscope optical axis.

The laser and its optical train are configured in a package which is generally quite sizeable and in certain circumstances interfere with the surgical procedure or with the movement of the microscope and its attached laser about the surgical field. Sometimes the laser will interfere with the view of the surgical site or will otherwise interfere with the access to the surgical site by the various personnel required to do the operation. Under some conditions a laser mounted at 90° to the optical axis offers advantages, while in other conditions, the parallel mounted laser provides advantages.

In the past, before compact lasers were mounted directly to the microscope, the laser was positioned remote from the microscope and the laser beam was delivered to the microscope through the articulated arm on which the microscope was supported. Such lasers are shown, for example, in U.S. Pat. No. 4,309,998 and U.S. Pat. No. 4,122,853. To permit transmission of the laser energy through the articulated arm, the arm must be hollow and a series of special joints and mirrors are used to deliver the beam to the surgical site. Every time the articulated arm is moved, there is a possibility that the lenses in the joints can become misaligned. If a large number of lenses are used the misalignments of the multiple lenses can require constant readjustment of the articulated arm and laser beam path.

It would be desirable to have a compact laser mounted directly to a microscope which could be swiveled from a position aligned perpendicular to the optical axis of the microscope to a position aligned parallel to the optical axis of the microscope or to a variety of other positions. It would further be useful to have such a swiveling laser mount which would not need constant realignment and adjustment of the lenses in the assembly.

SUMMARY OF THE INVENTION

The present invention provides a microscope attachment assembly for pivotably mounting a surgical laser head relative to a microscope. The assembly includes a microscope platform and mounting apparatus, which preferably mates with the existing dovetail bracket of the typical microscope. An opening in the microscope platform is aligned with the objective lens of the microscope so that when the microscope is mounted on the platform the user has an unobstructed view of the surgical site below the microscope. A first collar extends from the platform. A second collar fits within the first collar and supports the laser. There are rotational locking apparatus on the first and second collars so that the laser may be selectively positioned at various rotational alignments with the optical axis of the microscope. There may also be an axial locking mechanism for preventing the two collars from moving axially with respect to one another.

In the preferred embodiment, the rotational locking means includes a series of detent balls on one collar and a series of detent recesses on a confronting surface of the other collar which cooperate to hold the collars in a desired rotational orientation with respect to one another.

The axial locking mechanism can be another series of detent balls fitting into one or more detent grooves on the collars. The length of the detent grooves could be aligned with the two preferred positions of the rotational locking means to provide a stop for preventing rotation beyond the preferred positions. In one position the laser is oriented parallel to the optical axis of the microscope. In the other position the laser is oriented perpendicular to the optical axis of the microscope.

To minimize the optical misalignment of the laser beam with the focusing lenses, the principle negative focusing lens is mounted in the second collar so that its position with respect to the laser beam does not change when the laser is swiveled with respect to the microscope platform. A second focusing lens is mounted in the first collar or in the microscope platform. The second lens is intended to match the focal point of the laser beam with that of the objective lens of the microscope. Also the second lens can be used to vary the size of the laser beam at the focal plane of the microscope. The principal negative focusing lens can also be used for the same purpose.

These and other features and advantages of the present invention will become apparent from the following detailed description of the preferred embodiments taken in conjunction with the following drawings.

DETAILED DESCRIPTION OF THE PREFERRED EMBODIMENT

Figure 2:
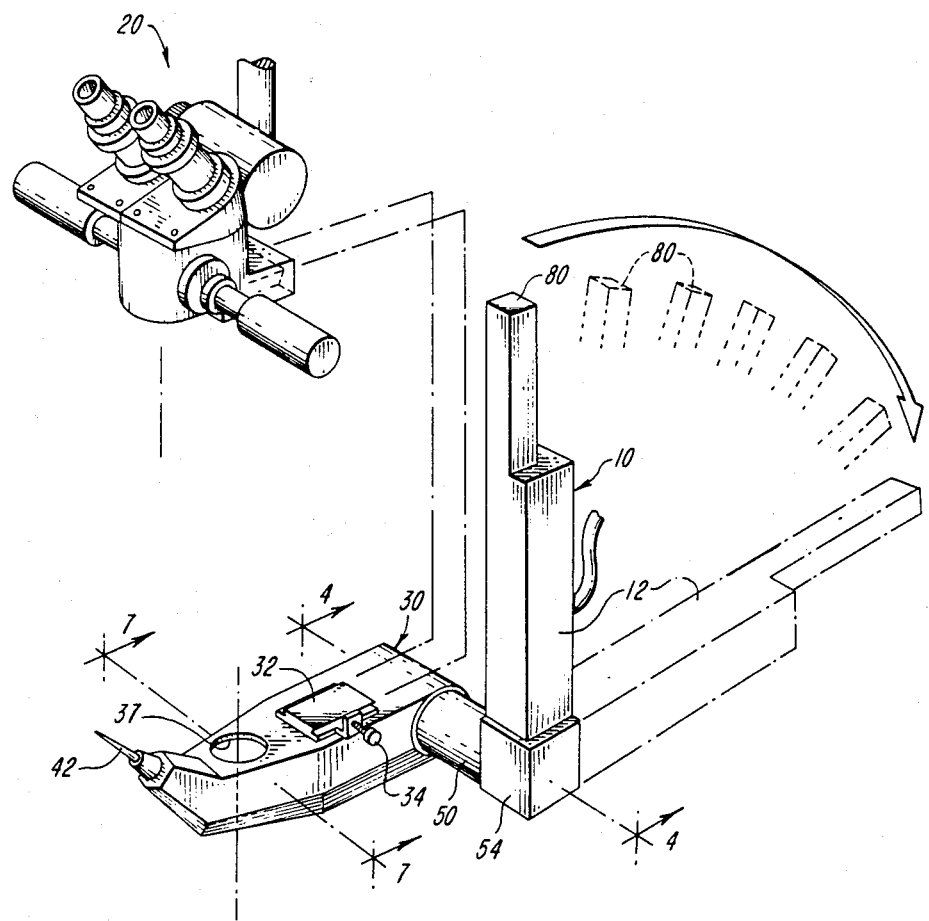
FIG. 2 shows an exploded perspective view of the microscope platform with the microscope and laser attached.
Figure 7:
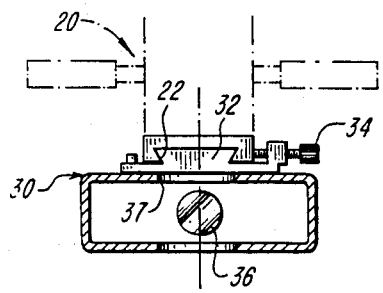
FIG. 7 is a partial cross-sectional view taken along line 7—7 in FIG. 2 showing the mounting of the microscope on the platform.

Referring concurrently to FIG. 2, there is shown a laser 10, a microscope 20, and a microscope platform 30. A standard microscope dovetail 22 (see FIG. 7) connects to a corresponding dovetail ways 32 on microscope platform 30. Dovetail locking screw 34 locks microscope 20 onto dovetail ways 32.

Figure 1:
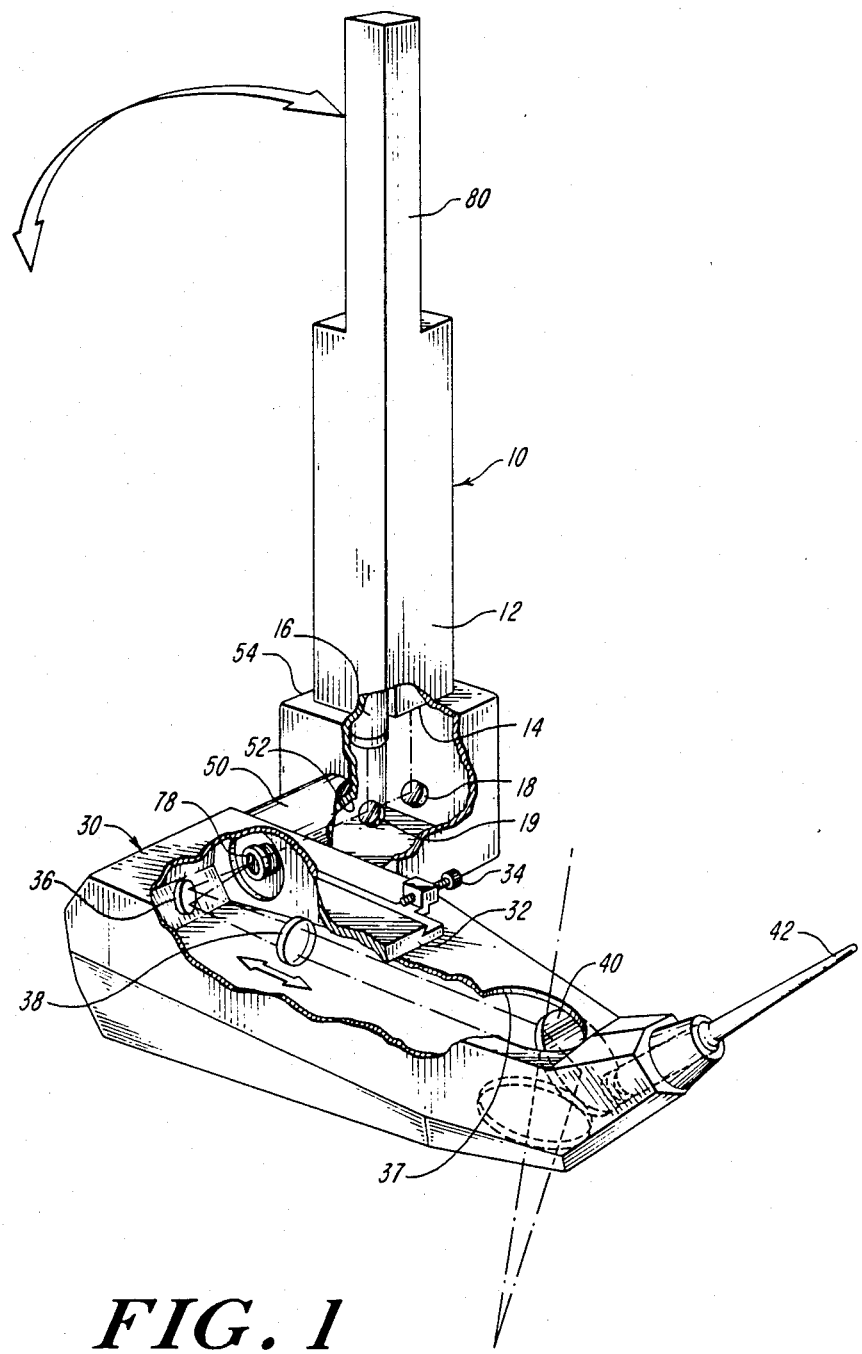
FIG. 1 shows a perspective view, partly in section of the present invention, the platform of the present invention with the laser attached and schematically showing major elements of the optical lenses used to transmit the laser beam through the platform with the laser aligned generally parallel to the optical axis of the microscope.

Referring now to FIG. 1, laser 10 is encased in laser housing 12 which encloses an operating laser 14, for example a carbon dioxide laser, and a targeting laser 16, for example a helium neon laser, with appropriate optics which can include a deflecting mirror 18 and a beam combiner 19 for jointly transmitting the helium neon and the carbon dioxide laser beams.

Microscope platform 30 encloses a deflecting mirror 36 and an adjustable field lens 38 which directs the laser beams onto an adjustable mirror 40. The mirror 40 can be manipulated by a manually operated joy stick 42 or alternatively could be adjusted automatically through a motor driven system (not shown).

Adjustable field lens 38 is intended to adjust the focal point of the laser beam to the focal length of the objective lens of the microscope so that the laser beam will be focused at the same focal plane that the surgeon views through the microscope. This lens is also preferably used to defocus the laser beam so that a variety of laser beam sites can be achieved at the focal plane of the microscope. Most microscopes are equipped with a variety of objective lenses so that the surgeon can adjust the working distance of the microscope from the surgical site. The adjustable field lens 38 must be correspondingly adjustable to different objective lens settings of the surgeon's microscope. Adjustable mirror 40 and joy stick 42 are used to direct the focused laser beam about the focal plane so that the laser beam may be moved during surgery to accomplish the various intended surgical procedures.

Still referring to FIG. 1 it can be seen that a first preferably cylindrical collar 50 extends from microscope platform 30 and receives a second preferably cylindrical collar 52 extending from the output end 54 of laser housing 12.

Figure 3:
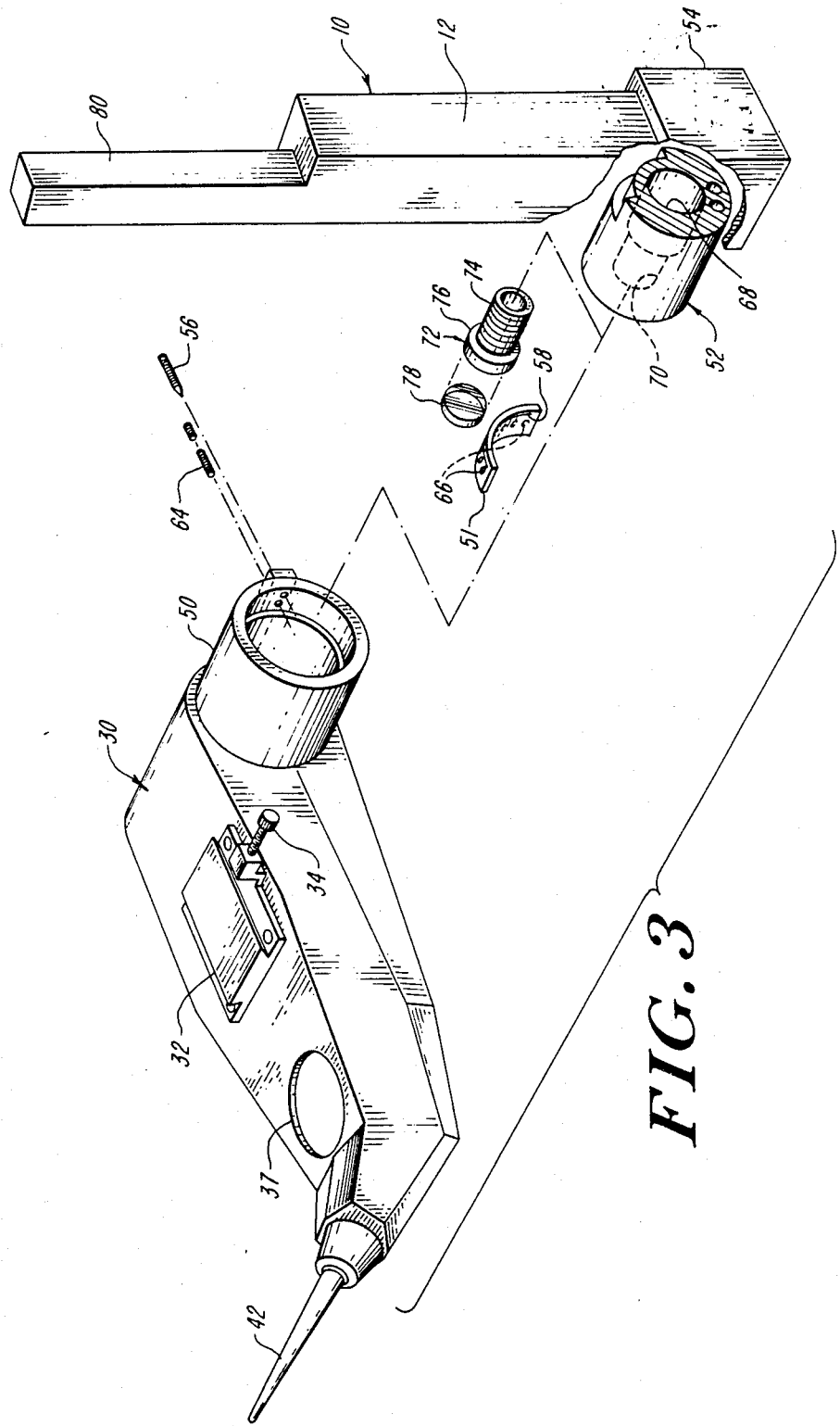
FIG. 3 shows an exploded perspective view of the present invention partly in section.

Referring now to FIG. 3, there is shown an exploded perspective of the microscope attachment assembly of the present invention including laser 10 and microscope platform 30 and showing details of the swivel mechanism associated with first collar 50 and second collar 52. A cone point set screw 56 is threaded through the wall of first collar 50. A slot 58 for receiving the end of set screw 56 is placed on the outside surface of rotary joint segment 51 and aligned with set screw 56. Preferably slot 58 extends 90° about the circumference of joint segment 51 and has end walls 60 and 62 (see FIG. 5) to act as stops in conjunction with set screw 56 to hold second collar 52 and laser 10 to which it is rigidly attached in either a parallel alignment with the optical axis of the microscope or in perpendicular alignment with the optical axis of the microscope. Also the interaction of set screw 56 with slot 58 prevents axially motion of collars 50 and 52 with respect to one another. Alternatively, the positions of set screw 56 and slot 58 could be reversed with set screw 56 being mounted on collar 52 or joint segment 51 and slot 58 being mounted on collar 50.

Still referring to FIG. 3, the preferred mechanism for locking laser 10 in various rotational positions with respect to microscope platform 30 is shown. Collar 50 includes a spring loaded detent ball 64 projecting through the wall of collar 50 at a point spaced axially apart from set screw 56 but preferably circumferentially adjacent set screw 56. A series of detent holes 66 project into the outside surface of rotary joint segment 51 aligned with detent ball 64. There are preferably six detent holes spaced equally angularly apart about a 90° arc of the circumference of segment 51. In the preferred embodiment there are six detent holes spaced 18° apart so that laser 10 may be locked in a variety of positions 18° apart from one another with respect to the optical axis of the microscope. Alternatively, the location of detent ball 64 and detent hole 66 could be reversed so that they appear respectively on segment 51 and first collar 50. Also the number and location of detent holdes 66 and the length of slot 58 can be changed to cover different angular increments.

Still referring to FIG. 3, we will now describe the mounting of the optical lenses within the microscope attachment assembly so as to minimize the misalignment of the optical lenses as the laser is swiveled from one position to another with respect to the optical axis of the microscope.

A portion of the interior surface 68 of second collar 52 contains threads 70. An annular lens mount 72 has corresponding threads 74 on its exterior circumferential surface. Lens mount 72 can be fixed in any position along the axially extent of threaded surface 68 by using well known locking mechanisms (not shown) but lens mount 72 will not extend axially into collar 52 any further than flange 76 permits. The position of lens mount 72 may be set in the factory and may be later adjusted in the field if necessary. A lens or lens system 78 is mounted in lens mount 72 by conventional means and is fixed in position in collar 52 with respect to laser 14 so that as laser housing 12 rotates from one position to another, lens 78 will stay in a fixed relationship with respect to the beams of lasers 14 and 16, deflector 18 and beam combiner 19 (see FIG. 1). Thus, misalignment of the optical path of the lasers during swiveling will be minimized.

The relationship between the laser beams and diverging lens 78 is extremely important for the proper alignment of the optical path. Having lens 78, which is typically a diverging lens, fixed with respect to the beam path of lasers 14 and 16 provides an important feature of the present invention which permits the laser to be swiveled with a minimum risk of misaligning the optical path. This is a significant improvement over passing the laser beam through a complexed optical path associated with the articulating arm assembly typical of many existing surgical laser systems.

Figure 4:
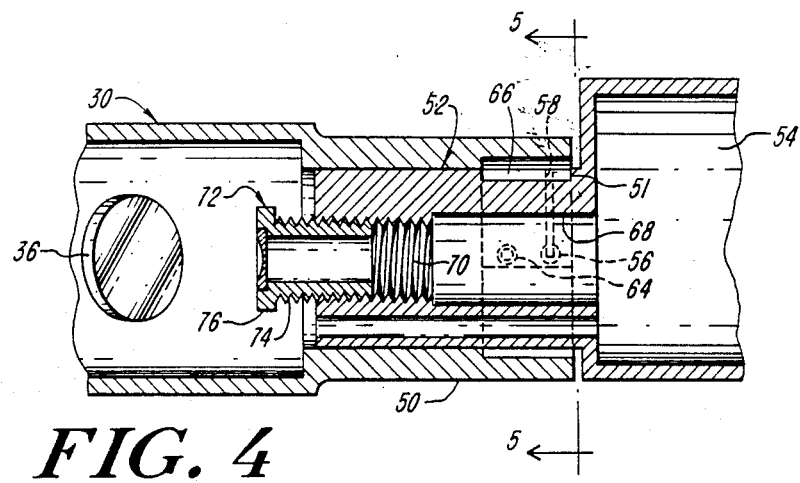
FIG. 4 shows a section view of the collars connecting the laser and microscope platform taken along line 4—4 in FIG. 2.
Figure 5:
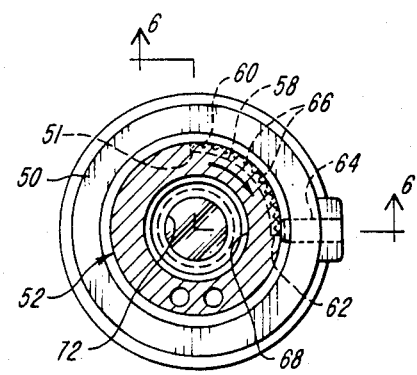
FIG. 5 is a cross-sectional view of the collar and lens arrangement of FIG. 4 taken along line 5—5 of FIG. 4.
Figure 6:
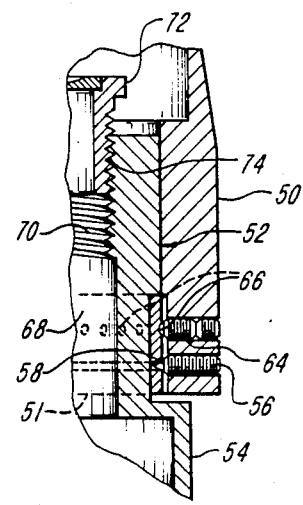
FIG. 6 is a partial cross-sectional view of the collars of FIGS. 4 and 5 taken along line 6—6 in FIG. 5 and showing the detent mechanism.

Referring to FIGS. 4 through 6, the preferred method for joining collars 50 and 52 is shown in cross-sectional detail. In FIG. 4 the second collar 52 is concentrically engaged inside the first collar 50. The lens mount 72 containing lens 78 is threaded into the interior 68 of the second collar 52. Lens 78 is thus seen to be aligned with deflecting mirror 36 in the platform 30.

FIG. 5 shows the concentric arrangement of collars 50 and 52, lens 78 and the laser beam path. The laser beam is directed through collars 50 and 52 and the center of lens 78, as explained in conjunction with FIG. 1. Collars 50 and 52 may move in a radial arc relative to each other, as delimited by the end walls 60 and 62 of the slot 58 into which set screw 56 extends. As collar 52 and laser housing 12 are rotated about the laser beam axis in collars 50 and 52, detent holes 66 and detent ball 64 provide detent position at discrete intervals around a rotational arc. Set screw 56 and spring loaded detent ball 64 are more clearly shown in FIG. 6, and are seen to be aligned with their respective slot and holes in the rotary joint segment 51. Alternatively, the entire detent mechanism can be replaced with friction rings (not shown) or a number of motorized means (not shown) and a number of other well known means for providing controlled rotation between two mating parts.

The coaxial alignment of collars 50 and 52 with the laser beam path, illustrated in FIG. 5, shows why the assembly of the present invention minimizes laser beam misalignment as the laser housing 12 is moved. Movement of laser housing results only in radial movement of the concentric collars 50 and 52. Since this movement is constrained to rotational pivoting about the laser beam path, there is no off-axis motion which can misalign the optical train, as there is when an articulated arm assembly with reflecting mirrors at the joints is moved.

In use the microscope attachment assembly of the present invention is mounted to an existing microscope 20 as shown in FIG. 2. The microscope is generally equipped with a microscope arm and counter balance system (not shown). With the microscope platform 30 attached to microscope 20 by means of dovetail groove 22, dovetail platform 32 and dovetail locking screw 34, the optical axis of the microscope will be generally aligned above opening 37 in platform 30. The adjustable field lens is adjusted to match the objective lens of the microscope so that the laser beam will be focused in the focal plane of the microscope objective lens. In FIG. 2 laser housing 12 is shown aligned generally parallel to the optical axis of the microscope. The user may conveniently move laser housing 12 to a different rotational position by grasping the projection 80 housing and pushing laser housing 12 away from him. The rotational locking mechanism which includes detent ball 64 and the series of detent holes 66 will hold laser housing 12 in a variety of rotational position (shown in phantom) between the two extremes of alignment parallel to or perpendicular to the optical axis of the microscope.

It will be noted that the optical path of the laser beam from lasers 14 and 16 will not change radially when laser housing 12 is rotated, but will merely pivot where the optical path passes through the concentric collars 50 and 52.

Thus, if the operating surgeon finds that the position of laser housing 12 is awkward or presents an obstacle to the surgical field, one can simply rotate laser housing 12 to a more convenient position. The optics will not change during the rotation and neither the laser optics nor the optics of the microscope need be adjusted. The rotation of laser housing 12 may be accomplished with minimal interruption and with maximum convenience.

It will be appreciated that the microscope attachment assembly of the present invention is particularly well suited to speedy and convenient adjustment of the orientation of laser housing 12 with respect to the optical axis of microscope 20. The adjustment can be accomplished with minimum interruption and minimum misalignment of the laser and visual optical paths so that surgical personnel can conveniently adjust the physical location of their instruments with minimum interruption during the surgical procedure.

The present invention has been described in conjunction with certain preferred embodiments. Those skilled in the art will appreciate that many modifications and changes may be made to the preferred embodiments without departing from the scope of the present invention. It is, therefore, not intended to limit the present invention except as set forth in the appended claims.

We claim:

1. An adjustable laser assembly for mounting a surgical laser to a surgical microscope over an operative area and for directing a surgical laser beam into the surgical field of the microscope, comprising:
   a microscope platform capable of receiving a laser beam at an entrance point and directing the beam through the microscope platform out to a desired point within the surgical field of the microscope;
   a laser housing rotatably connected at a laser beam exit to the entrance point of the microscope platform, wherein the laser housing has a longitudinal axis and the laser beam exit has an axis perpendicular to the longitudinal axis, and wherein the laser housing is free in space with respect to the microscope platform and can rotate in an arc around the axis of the laser beam exit to be positioned with respect to the microscope platform in a selected location on the arc without disturbing during rotation the alignment of a laser beam passing from the laser beam exit of the laser housing to the entrance point of the microscope platform;
   a surgical laser disposed within the laser housing and capable of generating a laser beam out of the laser housing along the axis of the laser beam exit; and
   a microscope mount attached to said microscope platform for rigidly mounting the microscope platform to the surgical microscope over the operative area.

2. The adjustable laser assembly of claim 1, wherein said microscope platform includes means for adjustably directing said laser beam to the desired point within the surgical field of the microscope.

3. The adjustable laser assembly of claim 2, wherein said means for adjustably directing said laser beam to the desired point within the surgical field of the microscope includes an adjustable mirror positioned in the path of said laser beam and a joy stick connected to the adjustable mirror for adjustment of the mirror to direct said laser beam to said desired point.

4. The adjustable laser assembly of claim 1, wherein said microscope platform includes means for adjusting the focal depth of said laser beam for varying depths of surgical field relative to the microscope platform.

5. The adjustable laser assembly of claim 4, wherein said means for adjusting the focal depth of said laser beam includes an adjustable field lens positioned in the path of said laser beam.

6. The adjustable laser assembly of claim 1, wherein said microscope platform includes a first annular collar extending from said microscope platform around said entrance point, wherein said laser housing includes a second annular collar extending from said laser housing around said laser beam exit, and wherein said first and second annular collars engage, one of said annular collars concentrically disposed within the other of said annular collars, to rotatably connect said laser housing to said microscope platform.

7. The adjustable laser assembly of claim 6, wherein said first and second annular collars include means cooperatively disposed on said annular collars for fixing said annular collars into position with respect to each other.

8. The adjustable laser assembly of claim 7, wherein said means for fixing said annular collars into position with respect to each other includes:
   a spring-loaded detent ball disposed on one of said annular collars; and
   a plurality of detent recesses disposed circumferentially on one surface of the other of said annular collars, and wherein said detent recesses are aligned with said detent ball and cooperate to fix said first and second annular collars at various rotational positions with respect to each other.

9. The adjustable laser assembly of claim 8, wherein said second annular collar is concentrically disposed within said first annular collar, wherein said spring-loaded detent ball is disposed on said first annular collar, and wherein said plurality of detent recesses are spaced about an arc on the outside circumferential surface of said second annular collar.

10. The adjustable laser assembly of claim 6, wherein said first and second annular collars include axial locking means cooperatively disposed on said first and second annular collars to prevent axial motion between said first and second annular collars.

11. The adjustable laser assembly of claim 10, wherein said axial locking means includes:
   a slot of a predetermined depth in said annular collar concentrically disposed within said other annular collar, wherein said slot circumferentially extends along the outside circumferential surface of said annular collar circumferentially disposed within said other annular collar;
   a set screw disposed in said other annular collar; and
   wherein said slot is aligned with said set screw to prevent axial motion of said first and second annular collars with respect to each other.

12. The adjustable laser assembly of claim 11, wherein said slot includes a first wall at one end of said slot and a second wall at the other end of said slot and wherein said first and second end walls provide stops against which said set screw may engage to set limits for the rotational position of said laser housing.

13. The adjustable laser assembly of claim 6, wherein said annular collar circumferentially disposed within said other annular collar includes:
   a lens mount adjustably disposed within said annular collar circumferentially disposed within said other annular collar; and
   a lens rigidly affixed to said lens mount.

14. The adjustable laser assembly of claim 13, wherein said annular collar circumferentially disposed within said other annular collar includes a threaded inside circumferential surface, wherein said lens mount is annular shaped and includes a threaded outside circumferential surface, and wherein said threaded outside circumferential surface of said lens mount cooperates with said threaded inside circumferential surface of said annular collar circumferentially disposed within said other annular collar to adjustably mount said lens mount within said annular collar circumferentially disposed within said other annular collar.

15. The adjustable laser assembly of claim 1, wherein said laser housing includes a handle portion to facilitate easy manipulation by a user.

16. A microscope attachment assembly for pivotably mounting a surgical laser housing to a microscope, comprising:
   a microscope platform;
   means on said microscope platform for affixing a microscope thereto;
   a laser housing;
   a first annular collar rigidly attached to and extending from said microscope platform;
   a second annular collar rigidly attached to and extending from said laser housing and engaging said first collar;
   rotational means cooperatively disposed on said first and second collars for selectively rotating and fixing into position said collars with respect to one another; and
   an axial locking means cooperatively disposed on said first and second collars for prohibiting axial motion between said first and second collars, wherein said axial locking means includes:
      a set screw mounted to said first collar;
      a slot extending circumferentially along said second collar at a predetermined depth thereinto; and
      wherein said slot is aligned with said set screw for receiving said set screw to prevent axial motion of said first collar with respect to said second collar.

17. The microscope attachment assembly of claim 16, wherein said slot extends circumferentially along the exterior surface of said second collar, wherein said slot further includes a first end wall at one end of said slot and a second end wall at the other end of said slot, and wherein said first and second end walls provide stops against which said set screw may engage to set limits for the rotational position of said laser housing with respect to said microscope platform.

* * * * *